(12) United States Patent
Cook

(10) Patent No.: US 12,058,998 B1
(45) Date of Patent: Aug. 13, 2024

(54) PERMEABLE AND SEMI PERMEABLE SUBSTRATE AND SUBSTANCE

(71) Applicant: Christina Rahm Cook, Brentwood, TN (US)

(72) Inventor: Christina Rahm Cook, Brentwood, TN (US)

( * ) Notice: Subject to any disclaimer, the term of this patent is extended or adjusted under 35 U.S.C. 154(b) by 113 days.

(21) Appl. No.: 17/500,075

(22) Filed: Oct. 13, 2021

Related U.S. Application Data

(60) Provisional application No. 63/198,351, filed on Oct. 13, 2020.

(51) Int. Cl.
| | |
|---|---|
| *A23L 33/16* | (2016.01) |
| *A01N 25/08* | (2006.01) |
| *A01N 59/00* | (2006.01) |
| *A01N 59/16* | (2006.01) |
| *A61K 33/00* | (2006.01) |
| *A61K 33/38* | (2006.01) |

(52) U.S. Cl.
CPC .............. *A01N 25/08* (2013.01); *A01N 59/00* (2013.01); *A01N 59/16* (2013.01); *A23L 33/16* (2016.08); *A61K 33/00* (2013.01); *A61K 33/38* (2013.01); *A23V 2002/00* (2013.01)

(58) Field of Classification Search
CPC .... A61K 33/06; A61K 2236/00; A61K 36/00; A61K 36/16; A61K 36/185; A61K 36/258; A61K 36/28; A61K 36/35; A61K 36/53; A61K 36/67; A61K 36/81; A61K 36/82
See application file for complete search history.

(56) References Cited

U.S. PATENT DOCUMENTS

2019/0151770 A1 * 5/2019 Mitchell ................ A61K 36/00

FOREIGN PATENT DOCUMENTS

| EP | 0444939 A1 * | 2/1991 | ............. A23L 33/15 |
| WO | WO-2016057057 A1 * | 4/2016 | ............. A23L 33/15 |

OTHER PUBLICATIONS

Waghmare, "Ultrasound assisted enzyme catalyzed hydrolysis of waste cooking oil under solvent free condition", Ultrasonics Sonochemistry, 32, pp. 60-67, 2016 (Year: 2016).*
Mody, "Feasibility of Using Nanofiltration as a Polishing Process for Removal of Cyanobacterial Exudates From Treated Surface Water Removal of Cyanobacterial Exudates From Treated Surface Water", USF Tampa Graduate Theses and Dissertations, 2004, pp. 1-118 (Year: 2004).*
Heard, "Fast room temperature lability of aluminosilicate zeolites", Nature Communications, 10:4690, pp. 1-7, 2019 (Year: 2019).*
Chen, "Effect of Ethanol on Ag@Mesoporous Silica Formation by In Situ Modified Stöber Method", Nanomaterials, 8, 362, pp. 1-14, 2018 (Year: 2018).*
Abbey Newsletter, "Zeolites", Abbey Newsletter, vol. 20, No. 7, Dec. 1996 (Year: 1996).*

* cited by examiner

*Primary Examiner* — Robert T. Crow
*Assistant Examiner* — John P Nguyen
(74) *Attorney, Agent, or Firm* — Gulf Coast Intellectual Property Group

(57) ABSTRACT

The present invention provides a permeable and options for semi-permeable inevitable substrate and substance made from minerals, vitamins, and detox formulas and is derived from the manufacturing process of the present invention. In one embodiment, the permeable inevitable substrate and substance may be used in clothing or other articles to be worn, in hospital settings, areas of nuclear waste, areas high in toxins, or areas of high radiation that may enable the radiation, the high energy levels and the toxins to activate the substrates and formulas that have been infused into clothing to self-clean and detox the clothing while it is being worn. In another embodiment, semi-permeable methods may be used by utilizing various forms of silicas and ortho silicates to ensure that positive molecules and ions are able to be diffused, while keeping out negative ions and minerals by diffusion or breaking apart the negative compositions.

1 Claim, 2 Drawing Sheets

PERMEABLE AND SEMI PERMEABLE SUBSTRATE AND SUBSTANCE

PRIORITY UNDER 35 U.S.C SECTION 119(E) & 37 C.F.R. SECTION 1.78

This nonprovisional application claims priority based upon the following prior United States Provisional Patent Application entitled: Permeable and/or Semi-permeable inevitable substrate and substance, Application No.: 63/198,351 filed Oct. 13, 2020, in the name of Christina Rahm Cook, which is hereby incorporated by reference for all purposes.

FIELD OF THE INVENTION

The present invention relates generally to environmental filtration, more specifically but not by way of limitation, a plurality of embodiments of objects such as but not limited to formulas and solutions thereof that can be applied to objects such as but not limited to articles of clothing that are operable to provide absorption or blocking of harmful materials such as but not limited to radiation, high energy levels and various toxins so as to inhibit exposure thereto by an individual.

BACKGROUND

Detoxification in areas where there are high levels of heavy metals, radiation, and toxins is problematic. Clothing exposed to heavy metals, radiation and toxins may be extremely difficult to clean. Simply washing these items in hot temperatures meant to kill viruses and bacteria often causes heavy metals, radiation, and toxins to expand or grow, combusting and coating the clothing, and the individuals wearing the clothing. Manual cleaning of clothing exposed to radiation and toxins is labor intensive and inefficient. Clothing fabric worn while being exposed to high energy levels, radiation, and toxins further exposes the skin, which is the largest organ of the body, to toxins, radiation, and high energy levels. Clothing, once taken off, is often destroyed in order to get rid of the toxins, radiation and energy, because if cleaned thoroughly, such clothing is likely damaged in the process.

There currently exists no effective way to clean radiation, high energy levels, or toxins from the body during exposure, or from clothing worn during exposure to prevent negative impact of radiation, energy, and toxins on the body, and to prevent negative impact of radiation, high energy levels or toxins on the clothing and on the environment. Also, there is not an effective option that exist that can determine and allow certain molecules or ions to pass through it by diffusion- or occasionally by more specialized processes of facilitated diffusion, passive or active transport while keeping other molecules and ions out using a semi-permeable format.

Accordingly, there is a need for a formulation and alternate embodiments thereof that can be employed in various applications such as but not limited to applying to clothing wherein the present invention results in a semi-permeable or permeable layer in order to inhibit passage of certain materials.

SUMMARY OF THE INVENTION

It is the object of the present invention to provide a formulation that is provided in various forms such as but not limited to a solution wherein the solution is applied to a substrate in order to enable the substrate to block materials from passing therethrough wherein the present invention employs various forms of silicas and ortho-silicates to ensure that positive molecules and ions are able to be diffused, while inhibiting passage of negative ions.

Another object of the present invention is to provide a solution that creates a semi-permeable layer on objects such as but not limited to clothing and further includes ingestible embodiments wherein the present invention includes an embodiment of an aqueous solution that utilizes a combination of silicas and ortho-silicates with mineral and vitamins attached as catalyst and carriers may be infused as a source of extra protection.

A further object of the present invention is to provide a formulation that is provided in various forms such as but not limited to a solution wherein the solution is applied to a substrate in order to enable the substrate to block materials from passing therethrough wherein the present invention includes an embodiment of a zeolite solution attached to silver or gold nanoparticles in the clothing and using the cage like structure, the clothing may be sprayed with various solutions that are capable of repelling insects, toxins, and antigens that are present in certain environments.

Still another object of the present invention is to provide a solution that creates a semi-permeable layer on objects such as but not limited to clothing and further includes ingestible embodiments wherein the present invention includes an oral formulation embodiment configured for ingestion by individuals to assist in immune system activation so as to promote the immune systems ability to fight against viruses, bacteria, fungus, parasites, antigens, toxins, and heavy metals.

An additional object of the present invention is to provide a formulation that is provided in various forms such as but not limited to a solution wherein the solution is applied to a substrate in order to enable the substrate to block materials from passing therethrough wherein the present invention includes an embodiment of detoxifying composition having a first inactive state and a second activated state wherein the activated state is capable of absorbing or neutralizing at least one harmful agent selected from radiation, toxins, energy radicals and combinations thereof.

Yet a further object of the present invention is to provide a solution that creates a semi-permeable layer on objects such as but not limited to clothing and further includes ingestible embodiments wherein the present invention may be provided in a liquid form, a solid form, a powder, an emulsion, a cream or a lotion and wherein the manufactured substance may be incorporated into fibers and fabrics. Furthermore, the present invention may be distributed in water, sprayed, inhaled, applied, or ingested.

Another object of the present invention is to provide a formulation that is provided in various forms such as but not limited to a solution wherein the solution is applied to a substrate in order to enable the substrate to block materials from passing therethrough wherein the present invention employs a fractionation process to facilitate manufacture of a liquid form thereof.

Still an additional object of the present invention is to provide a solution that creates a semi-permeable layer on objects such as but not limited to clothing and further includes ingestible embodiments wherein the present invention includes solutions of zeolite, silicate, silver ions at least a 95% concentration in order for the solution to execute its intended functionality in the clothing application.

Yet another object of the present invention is to provide a formulation that is provided in various forms such as but not limited to a solution wherein the solution is applied to a substrate in order to enable the substrate to block materials from passing therethrough wherein the present invention includes a process for manufacture and activation of the formulation of the present invention wherein the ambient temperature is between eight and twenty six degrees Celsius.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

DETAILED DESCRIPTION

Figure 1:
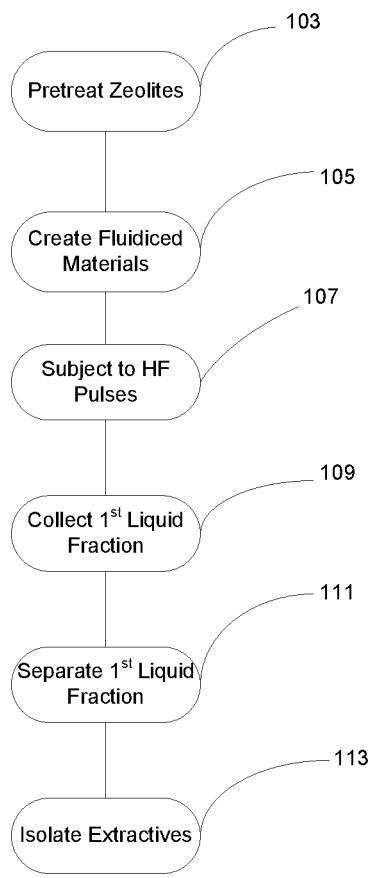
FIG. 1 is an outline of an exemplary process of the present invention.

Referring now to the drawings submitted herewith, wherein various elements depicted therein are not necessarily drawn to scale and wherein through the views and figures like elements are referenced with identical reference numerals, there is illustrated a formulation 100 constructed according to the principles of the present invention.

An embodiment of the present invention is discussed herein with reference to the figures submitted herewith. Those skilled in the art will understand that the detailed description herein with respect to these figures is for explanatory purposes and that it is contemplated within the scope of the present invention that alternative embodiments are plausible. By way of example but not by way of limitation, those having skill in the art in light of the present teachings of the present invention will recognize a plurality of alternate and suitable approaches dependent upon the needs of the particular application to implement the functionality of any given detail described herein, beyond that of the particular implementation choices in the embodiment described herein. Various modifications and embodiments are within the scope of the present invention.

It is to be further understood that the present invention is not limited to the particular methodology, materials, uses and applications described herein, as these may vary. Furthermore, it is also to be understood that the terminology used herein is used for the purpose of describing particular embodiments only, and is not intended to limit the scope of the present invention. It must be noted that as used herein and in the claims, the singular forms "a", "an" and "the" include the plural reference unless the context clearly dictates otherwise. Thus, for example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

References to "one embodiment", "an embodiment", "exemplary embodiments", and the like may indicate that the embodiment(s) of the invention so described may include a particular feature, structure or characteristic, but not every embodiment necessarily includes the particular feature, structure or characteristic.

The present invention provides a formulation created by the manufacturing process described herein that includes silver ion, silica, and zeolite formulas that are hydrolyzed or that use nanotechnology employing the process of fractionation and extraction in order to isolate extractions for pharmaceuticals and nutraceuticals to be utilized for the environment and for humans and animals. Silver ions, zeolites, and silicas and their isolates are of particular interest in the fields of nutraceuticals, pharmaceuticals, medical supplies, and disinfectants for treating bacteria, viruses, parasites, diseases, illness bacteria, heavy metals and environmental remediation. However, existing technologies are not completely effective in isolating and collecting extractives from silver ions, zeolites, and silicas.

The present invention provides manufacturing and development techniques that involve fractionation, extraction and various cryogenic thermal fracturing of compounds and compositions comprised of silicas, orthosilicates, amphibiolesilicates, and phyllo silicates and mixtures thereof. The compounds and compositions may be used with or may be derived from various materials including but not limited to silver ions, zeolites, zeolite materials and combinations thereof, to isolate extractives. The extractives may comprise or be incorporated into pharmaceutical products, nutraceutical products, environmental products, medical devices, protective clothing. The extractives may include various minerals and vitamins including but not limited to Vitamin C, Zinc, Niacin, Vitamin Ds, Vitamin D3, Selenium, Vitamin B group, Melatonin, Quercetin, Palmitoylethanolamide (PEA), Specialized Pro-Resolving Mediators (SPMs), Curcumin, Epigallocatechin Gallate (ECGG), Resveratrol, Black Cumin and any combination of the foregoing. The extractives are further utilized to improve efficacy and safety of products into which they are integrated. The process of the present invention utilizing fractionation and extraction of silicas in their basic form or in combination of other formulas in development and manufacturing, may produce pharmaceuticals, nutraceuticals, medical products, clothing and environmental products to improve the efficacy, safety and deliverability.

One embodiment of the present invention provides a process of fractionation and extraction of ions, elements and compounds selected from silicas, silver ions, zeolites, zeolite materials and combinations thereof and isolates extractives for the formulation 100 to be integrated into nutraceutical and pharmaceutical compositions. Furthermore, in addition to the extractives produced by the process of the present invention an emphasis on manufacturing that involve fractionation, extraction and various cryogenic thermal fracturing techniques of compounds and compositions comprising silicas, orthosilicates, amphibiole silicates, and phyllo silicates and mixtures thereof. The formulation 100 may be utilized with or may be derived from various materials including but not limited to silver ions, zeolites, zeolite materials and combinations thereof, to isolate extractives.

In accordance with an exemplary embodiment of the present invention, an inventive process including one or more steps of fractionation and extraction of ions, elements and compounds selected from silver ions, silicas, and zeolites is provided. In some embodiments of the present invention the ions, elements and compounds may be fractionated or extracted alone or in combination with various oils, vitamins, and minerals added to provide isolated extractives. The process further provides isolated extractives, which may effectively protect the body and environment against bacteria, viruses, fungi, and parasites that are known to impact the body relative to its vulnerability to disease and illness. Additionally, the formulation will effectively assist with remediation and detoxification of the aforementioned. The present invention is directed to the isolated extractives produced by the inventive process described herein. In another exemplary embodiment the present invention provides a process for fractionating and/or extracting silver ions, silicas, and zeolites alone or in combination with various oils, vitamins, and minerals added, to provide isolated extractives.

In yet another exemplary embodiment of the present invention examples of the following types of compositions may be produced: nutraceutical supplements for animals, nutraceutical supplements for people, supplements for the land, air, and water, and over the counter products to assist with treatment of supporting the body while taking vaccines and exposure to items such as but not limited to nuclear waste and heavy metals. Further, in an exemplary embodiment, compositions according to the present invention may be used to develop vaccines, scaffolds, drugs, and other biotech compositions in the pharmacological and biotechnology fields. Following are conditions or other parameters that exist in the preferred embodiment of the present invention. During the process of the present invention the ambient temperature is between '8 to 26 degrees Celsius. Solvents utilized during the process are 50-95% aqueous ethanol, and/or oils from plants. During the process of the present invention the high frequency pulses are at least 1000 pulses per second. During the process for fractioning the zeolite, silica, and/or silver ion materials additional materials to be utilized may include but are not limited to: curcumin oil, turmeric oil, resveratrol, black cumin oil, raspberry oil, oregano oil, tea tree oil, black pepper oil, L-Arginine, L Theanine, 5HTP, vitamins A, B, C, D, E, K, Zinc, Folate, olive leaf extract, seasalt, garlic, avocado oil, grape seed oil, coconut oil, almond oil, olive oil.

Referring now to FIG. 1, in step 103 pretreating the zeolites, silicas, and silver ions to provide fluidized materials is executed employing suitable techniques. While not illustrated in the diagrams submitted as a part hereof, it should be understood within the scope of the present invention that hypochlorous acid(HOCL), which is formed by dissolving water in chlorine is utilized in the process of the present invention. Hypochlorous acid partially disassociates forming hypochlorite and is desired to be utilized in the process discussed herein. Step 105 consists of subjecting the pretreated fluidized zeolite, silica, and silver ion to simultaneous high frequency pulses and shear forces without denaturing bioactive properties of one or more bioactive components of the silver ion, silica, or zeolite materials to provide a first liquid fraction having extractives to be isolated and a first fractionated silver ion, silica, and zeolite formula alone or combination thereof. It should be understood within the scope of the present invention that the high frequency pulses are between 300 pulses per second and about 200 pulses per second. In step 107, separation of the first liquid fraction having extractives from the first fractionated silver ion, silica, and/or zeolite material is executed.

It should be understood within the scope of the present invention that this comprises force applied to the first fractionated materials of zeolite, and/or silicas, and/or silver ions alone or in combination with each other 109 isolating extractives from the first liquid fraction. Further more wherein isolation compromises contacting the first liquid having extractives with a membrane for selectively isolating the extractives based on molecular weight. In step 111, the materials are put into *E-coli*, yeast, or mammalian host cells.

Figure 2:
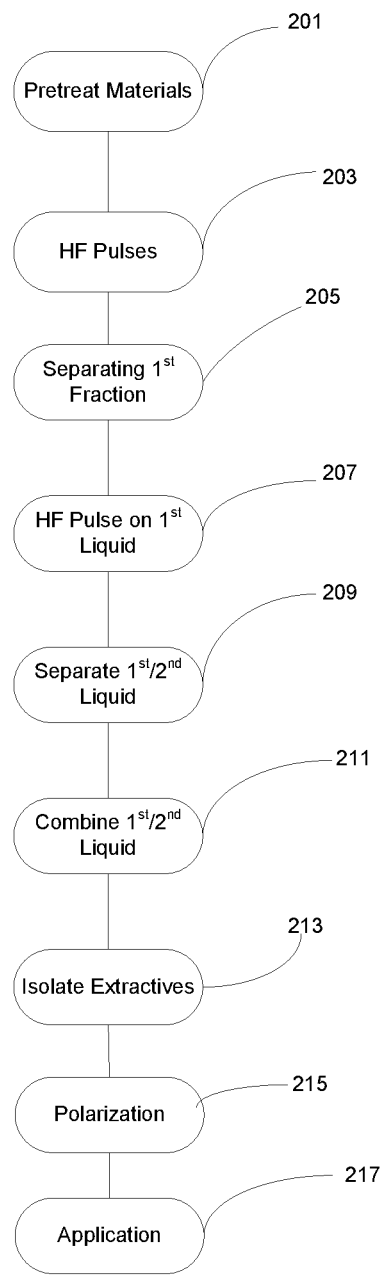
FIG. 2 is an outline of an exemplary process of the present invention.

Referring now to FIG. 2 submitted as a part hereof, in step 201 pretreating the materials by soaking in a solvent to provide fluidized plant materials. In step 203 includes subjecting the pretreated fluidized materials to high frequency pulses. Step 205 consists of separating the first liquid fractionated material, In step 207, the process of the present invention provides subjecting the first fractionated material to the same high frequency pulses and shearforces of step 203 so as to provide a second liquid fraction having extractives to be isolated from the second liquid. In step 209, the process includes separating the second fractionated liquid fraction having extractives to be isolated from the second fractionated materials. Step 211 includes combining the first liquid fraction with the second liquid fraction. In step 213 the process of the present invention includes isolating the extractives from the combined first liquid fraction and second liquid fraction and wherein the step of isolating comprises the first liquid fraction and the second liquidfraction being passed through a membrane. Step 215 includes execution of a polarization process so as to separate positive and negative ions. In step 217, the end polarized product is finalized for an end product embodiment wherein the end product embodiments are discussed herein.

An exemplary embodiment of the present invention may provide a process of fractionating and/or extracting zeolites, silicas, and silver ions, along or in combination, with various, oils, vitamins, minerals, and other elements used as catalyst. Additionally, the present invention may be readily adaptable for large-scale production but may be used to further research in the aspects of *E-coli* host, yeast cell host, and mammalian cell host for the use in treating various autoimmune disorders, viruses, bacteria, fungi, and parasitesin people, animals, and the environment. The embodiments of the present invention are listed in detail but do not have to be followed in order or sequence.

A preferred embodiment of the present invention provides a permeable and options for semi-permeable inevitable substrate and substance made from process described herein. In one embodiment, the permeable substrate and substance is utilized in clothing or other articles to be worn, in hospital settings, areas of nuclear waste, areas high in toxins, or areas of high radiation wherein the radiation, high energy levels or toxins provide activation of the formulation 100 that has been infused into clothing or other articles of apparel. In another embodiment, semi-permeable methods are utilized wherein various forms of silicas and ortho silicates are employed to ensure that positive molecules and ions are able to be diffused, while keeping out negative ions and minerals by diffusion or breaking apart the negative compositions so they no longer pose a threat. Furthermore, in a third embodiment, an aqueous solution using a combination of silicas and ortho silicates with mineral and vitamins attached as catalyst and carriers may be infused as a source of extra protection. These formulas may be applied to the clothing, and may utilize silver and gold nano-particles attached to the clothes to adhere to the solution and disperse appropriately depending on the anticipated antigen or toxin.

The manufactured embodiments of the present invention may be administered, sprayed, inhaled, applied or ingested. The manufactured formulation 100 of the present invention may be incorporated into fabric, clothing, oils, foods, minerals, and vitamins and will be activated by the radiation, toxins and energy radicals. Furthermore, the aqueous solution of the present invention may be sprayed on the skin or on clothing to protect the skin from viruses, bacteria, fungus, parasites, toxins, heavy metals, antigens, and toxins, to protect the skin under the clothing so as to not initiate further aging and destruction due to the harm the aforementioned can cause to the skin and body. Fabric infused with various types of detox products centered around silicates and solutions, including, but not limited to silver ions, silicates, zeolites, lavender oils, oregano oils, turmeric oil, black seed oil, olive leaf oil, and any oil or substance that may be further activated by radiation, high amounts of heat or temperature, toxins and combinations thereof. Fabric interwoven by silver nanoparticles that are heat and radioactively activated so they may act as an antibacterial agent, nanoparticle-based transparent sunscreen, carbon fiber strengthening using slice nanoparticles.

The fabric of cotton, hemp or other synthetic and natural substances can be utilized with the formulation 100 of the present invention. The solutions of zeolite, silicate, silver ions may be at least a 95% concentration when the process initiates so that the formulas may be strong enough to work in the clothing lines in order to provide the desired effects.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A formulation method operable to produce a formulation capable of being distributed in water, sprayed, inhaled, applied, or ingested in order to provide protection from harmful agents wherein the formulation method comprises the steps of:
    pretreating materials by soaking in hypochlorous acid to provide fluidized plant materials;
    subjecting the fluidized plant materials to high frequency pulses so as to create extractives, wherein the high frequency pulses occur at a rate of 250 per second;
    separating a first liquid fractionated material from the fluidized plant materials;
    subjecting the liquid fractionated material to high frequency pulses and shearforces to provide a second liquid fraction having the extractives to be isolated from the second liquid fraction;
    separating the second liquid fraction having the extractives to be isolated from second fractionated materials;
    combining the first liquid fraction with the second liquid fraction;
    isolating the extractives from the combined first liquid fraction and second liquid fraction and wherein the first liquid fraction and the second liquid fraction are engaged with a membrane.

* * * * *